US00PP28521P2

(12) United States Plant Patent
Hansen

(10) Patent No.: US PP28,521 P2
(45) Date of Patent: Oct. 10, 2017

(54) ***COREOPSIS* PLANT NAMED 'CURRY UP'**

(50) Latin Name: *Coreopsis verticillata*
Varietal Denomination: Curry Up

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/330,029

(22) Filed: Jul. 27, 2016

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette Para

(57) ABSTRACT

The new and distinct threadleaf *coreopsis* plant, *Coreopsis verticillata* plant named 'Curry Up', with narrowly-linear, deeply-dissected, typically 3 to 5-lobed foliage of gray-green, numerous flowers of clear golden yellow petals with dark red eyes over a prolonged flowering season from early summer until late summer.

1 Drawing Sheet

Botanical designation: *Coreopsis verticillata.*
Cultivar denomination: 'Curry Up'.

BACKGROUND OF THE PLANT

The present invention relates to the new and distinct threadleaf *coreopsis* herein also referred to as *Coreopsis* 'Curry Up', by the cultivar name, 'Curry Up', or as the new plant. The new plant was selected by the inventor in June of 2012 from an isolated block of plants all derived from the seedling with breeder code HK10-06-01 (not patented) which is a seedling of *Coreopsis* 'Route 66' U.S. Plant Pat. No. 20,609 collected in the summer of 2011 from a proprietary unreleased seedling identified with the in the fields of a wholesale perennial grower based in Zeeland, Mich., USA. It was then isolated and compared in subsequent years to other *coreopsis* and subsequently found to be different from all cultivars known to the discoverer.

Asexual propagation at the same nursery in Zeeland, Mich., USA by cuttings has shown 'Curry Up' to be stable and reproduce true to type in successive generations.

No plants of *Coreopsis* 'Curry Up' have been sold, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

SUMMARY OF THE PLANT

*Coreopsis* 'Curry Up' has not been observed in all possible environmental conditions. The phenotype may vary slightly with changes in environments such as light intensity, fertility, water availability, etc. without, however any variation in genotype.

*Coreopsis* 'Curry Up' is distinct from all cultivars known to the inventor in the following traits:

1. Narrow foliage with compact height and dense habit.
2. Heavy flowering with ray petals of clear golden yellow with dark red eyes.

3. Flowers produced tightly and densely above the bright-green thin foliage.
4. Long flowering period beginning with concentration in mid-June and continuing until late summer.

Plants of *Coreopsis* 'Curry Up' are most similar to 'Firefly' U.S. Plant Pat. No. 26,295, 'Bengal Tiger' U.S. Plant Pat. No. 25,345, 'Sunset Strip' U.S. Plant Pat. No. 22,670 and 'Red Shift' U.S. Plant Pat. No. 20,412. 'Red Shift' produces ray flower petals that have a narrower red eye with more purple coloration at the base and distal portion is lighter yellow than the more golden yellow and larger burgundy eye of 'Curry Up'. The ray petals of 'Sunset Strip' are more orange on the distal portion and more reddish orange in the eye than the new plant. The distal portion of the ray petals of 'Bengal Tiger' is a lighter yellow than that of 'Curry Up', and the eye of the former is wider or larger than the new plant. The habit of 'Bengal Tiger' is also shorter and wider than that of 'Curry Up'. 'Firefly' is much shorter and narrower than 'Curry Up' in habit. No plants of the female parent were saved, so no mature plant comparison could be made.

BRIEF DESCRIPTION OF THE DRAWINGS

The color drawings illustrate the overall characteristics of *Coreopsis* 'Curry Up' as a three-year-old plant. The colors are as true as reasonably possible given the technology available. The color values may vary slightly depending on light intensity and quality.

DETAILED BOTANICAL DESCRIPTION

Figure 1:
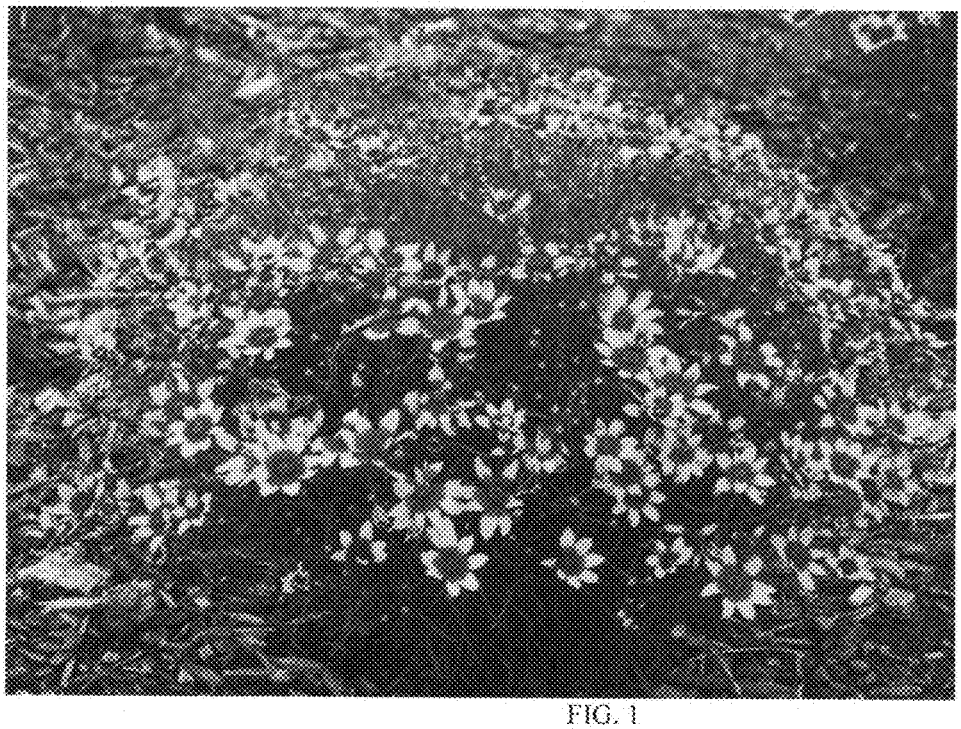
FIG. 1 shows the new plant in a landscape environment.
Figure 2:
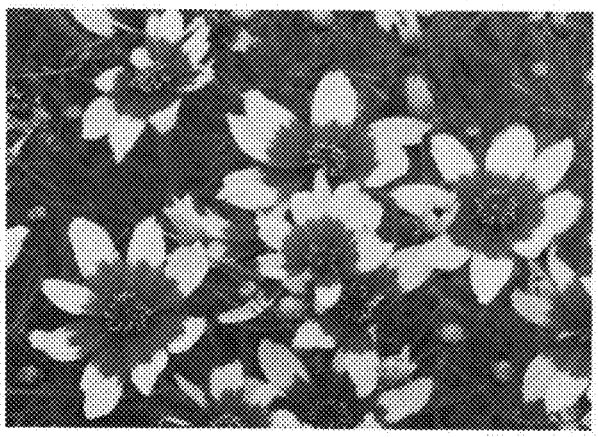
FIG. 2 shows a close-up of the flowers of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2001 edition.

Parentage: Female or seed parent HK10-06-01 (not patented); male or pollen parent unknown.

Asexual propagation: Cuttings, about 10 to 14 days to initiate roots; time to finish as # 1 field grown size about 9 months.

Plant habit: Dense axillary branches; rounded, herbaceous perennial mound; up to 72 cm wide and 52 cm tall; average about 60 cm across and 42 cm tall.

Leaves: Opposite, entire, glabrous; deeply dissected, irregularly lobed, typically tri to penta-lobed, acute apex; base attenuate; sessile; up to 11.5 cm long and 10.5 mm wide, average about 5.5 cm long and 5.5 cm wide; lobes to 6.5 cm long and 3.0 mm across.

Leaf color: Young expanding leaves adaxial nearest RHS 137B and abaxial nearest RHS 137C; mature leaves adaxial nearest RHS 137A, abaxial nearest RHS 137B.

Veins: Pinnate; only abaxial midvein obvious.

Abaxial midveins color: Same as surrounding leaf.

Flower: Composite consisting of ray and disk florets; on terminal branches; about 4.0 cm diameter, about 1.2 cm tall from lower involucral bracts to top of disk florets; attitude upright to outwardly.

Flower fragrance: Not detected.

Phyllary: Sepals in two distinct whorls, outer or lower set consisting of about ten, acute apex, narrowly deltoid, truncate base, glabrous, to about 3.2 mm long and 1.5 mm wide at base; inner or upper set tight against ray petals, usually eight in number, about 5.0 mm long and about 3.5 mm wide, deltoid to ovate; acute apex and truncate base.

Phyllary color: Lower set nearest RHS 137A on both surfaces with lighter margin of nearest RHS 145D; upper set nearest RHS 144A in proximal and central portion of both abaxial and adaxial, marginally and distally nearest RHS 26A.

Flowering period: Early summer until late summer, for about 10 weeks; producing over 40 flowers per stem and over 200 flowers per plant.

Flower longevity: 4 to 6 days.

Flower buds: One to two days before showing ray petal color spherical with slightly flattened top, 4.0 mm wide and 5.0 mm tall.

Flower bud color: Base nearest RHS 137A and apex nearest RHS 163A.

Stem: Terete; glaucous, thin, wiry, upright attitude, strong, many branched; 4.0 mm wide at base and 33.0 cm long; about seven nodes, average internode spacing about 4.7 cm.

Stem color: Nearest RHS 138A.

Peduncle: Terete; glaucous, thin, wiry, strong; average about 0.5 mm in diameter, 3.0 cm long.

Peduncle color: Nearest RHS 138A.

Pedicel: Absent.

Ray florets: Imperfect; staminate.

Ligule: Usually 8 per flower; oblong elongate, glabrous; apex typically two-notched, margin entire; base narrowly cuneate to attenuate; opening nearly flat to form about 180° angle; parallel veined; glabrous adaxial and adaxial; about 2.0 cm long and about 8.0 mm wide; basal corolla tube about 1.5 mm to 3.0 mm long and about 0.8 mm diameter; lacking stamens and pistils.

Ligule color: Adaxial basal one-third nearest RHS 53A, adaxial distal two-thirds nearest RHS 15A; abaxial nearest RHS 14B with greyed-orange undertones of nearest RHS 176C in basal one-third.

Disk florets: 20 to 40 per head; consisting of fused petal tube; perfect; size about 6.0 mm long by 1.0 mm wide at top.

*Petals*.—Five; 5 mm long and 1 mm wide, fused in the basal 4 mm, acute apex.

*Petal color*.—Adaxial nearest RHS 187B distally and between RHS 151D and RHS 153D proximally, abaxial nearest RHS 175B distally and nearest RHS 161B proximally.

*Staminal tube*.—Made up of five fused stamens, 3 to 4 mm long.

*Anther*.—About 1 mm long, nearest RHS N186A.

*Pollen*.—Fine, round, closest to RHS 23A.

*Style*.—About 5.0 mm long; nearest RHS 160C at base, between RHS 22A and RHS 22B distally.

*Stigma*.—Split in half and curling back as it matures; color nearest RHS 21A.

Seed: Linear with slight curve, with acute apex and truncate base; glabrous abaxial and adaxial surfaces, margin ciliolate; about 4.5 mm long, about 1.7 mm across and about 0.5 mm thick.

Seed color: Variable, nearest RHS 202A. *Coreopsis verticillata* 'Curry Up' is tolerant of winter temperatures as low as −20° C. and summer temperatures as high as 40° C. Once established it is also tolerant of dry summer conditions but does best with ample moisture and good drainage. It is not known to be resistant of diseases and pest that are common to other *Coreopsis* cultivars.

I claim:

1. The new and distinct cultivar of *Coreopsis* plant named 'Curry Up' as described and illustrated and useful as a specimen landscape plant, mass planting or cut flower.

* * * * *